United States Patent
Anzai et al.

(10) Patent No.: US 11,702,638 B2
(45) Date of Patent: Jul. 18, 2023

(54) CELL CULTURE SUBSTRATE HAVING AN ACRYLATE STRUCTURAL UNIT AND A MONOMER STRUCTURAL UNIT

(71) Applicant: TERUMO KABUSHIKI KAISHA, Tokyo (JP)

(72) Inventors: Takao Anzai, Kanagawa (JP); Ichiro Hirahara, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 617 days.

(21) Appl. No.: 16/541,989

(22) Filed: Aug. 15, 2019

(65) Prior Publication Data

US 2020/0056155 A1  Feb. 20, 2020

(30) Foreign Application Priority Data

Aug. 16, 2018 (JP) ................. 2018-153269

(51) Int. Cl.
*C12N 5/0775* (2010.01)
*C12M 1/00* (2006.01)

(52) U.S. Cl.
CPC .......... *C12N 5/0667* (2013.01); *C12M 23/20* (2013.01); *C12N 2533/00* (2013.01)

(58) Field of Classification Search
CPC .. C12N 5/0068; C12N 2533/30; C12M 23/20; C12M 25/14
See application file for complete search history.

(56) References Cited

U.S. PATENT DOCUMENTS

| | | | | |
|---|---|---|---|---|
| 3,726,943 A * | 4/1973 | Joy | ......... | C08G 77/48 556/439 |
| 6,225,367 B1 * | 5/2001 | Chaouk | ........ | G02B 1/043 528/367 |
| 8,354,274 B2 * | 1/2013 | Fadeev | ........... | C12N 5/0606 435/174 |
| 8,603,820 B2 * | 12/2013 | Martin | ........... | C12N 5/0068 435/402 |
| 9,115,238 B2 * | 8/2015 | Deshayes | ........... | C08F 2/32 |
| 2011/0207219 A1 * | 8/2011 | Bookbinder | ........ | C12N 5/0068 435/402 |
| 2012/0295353 A1 * | 11/2012 | Hong | .............. | C08F 220/20 435/402 |
| 2014/0370598 A1 * | 12/2014 | Colton | ................ | C12N 5/0068 435/377 |
| 2015/0191693 A1 * | 7/2015 | Ameringer | .......... | C12M 25/06 427/508 |

FOREIGN PATENT DOCUMENTS

| | | | | |
|---|---|---|---|---|
| EP | 2598518 A1 * | 6/2013 | ............ | C07K 14/78 |
| JP | 2011-510655 | 4/2011 | | |
| JP | 2013-535200 | 9/2013 | | |
| WO | WO-2012014003 A1 * | 2/2012 | ............ | C07K 14/78 |

OTHER PUBLICATIONS

Lerman et al. The Evolution of Polystyrene as a Cell Culture Material. Tissue Engineering Part B (2018), 24(5), 359-372. (Year: 2018).*
Melkoumian et al. Synthetic peptide-acrylate surfaces for long-term self-renewal and cardiomyocyte differentiation of human embryonic stem cells. Nature Biotechnology (2010), 28(6), 606-610 plus appended Online Methods. (Year: 2010).*
Patel et al. A defined synthetic substrate for serum-free culture of human stem cell derived cardiomyocytes with improved functional maturity identified using combinatorial materials microarrays. Biomaterials (2015), 61, 257-265. (Year: 2015).*
Kim et al. Synthesis and characterization of in situ chitosan-based hydrogel via grafting of carboxyethyl acrylate. J Biomed Mater Res (2007), 83A, 674-682. (Year: 2007).*
Sato, Chicako; Aoki, Mahiko; Tanaka, Masaru; "Blood-compatible poly (2-methoxyethyl acrylate) for the adhesion and proliferation of endothelial and smooth muscle cells", Colloids and Surfaces B: Biointerfaces, Elsevier B.V. May 18, 2016, pp. 586-596.
Official Action (with English translation) for Japan Application No. 2021-502909, dated May 23, 2023, 10 pages.

* cited by examiner

*Primary Examiner* — Sean C. Barron
(74) *Attorney, Agent, or Firm* — Sheridan Ross P.C.

(57) ABSTRACT

This invention is to provide a means capable of obtaining excellent cell proliferation activity without depending on a thickness of a coating layer in a technique of coating a cell culture substrate (cell culture vessel) using a polymer. Provided is a cell culture substrate comprising a coating layer on at least one surface of a polymer substrate, wherein the coating layer includes a copolymer comprising more than 40% by mole and less than 100% by mole of a structural unit (1) derived from carboxyalkyl (meth)acrylate represented by Formula (1) and more than 0% by mole and less than 60% by mole of a structural unit (2) derived from ethylenically unsaturated monomer having a hydroxyl group (the total of the structural unit (1) and the structural unit (2) is 100% by mole).

10 Claims, 2 Drawing Sheets

CELL CULTURE SUBSTRATE HAVING AN ACRYLATE STRUCTURAL UNIT AND A MONOMER STRUCTURAL UNIT

TECHNICAL FIELD

The present invention relates to a cell culture substrate excellent in cell proliferation activity, and a bioreactor and a method for culturing a stem cell using the cell culture substrate.

BACKGROUND

In recent years, a cell culture technology has been used in the development of regenerative medicine or drug discovery. In particular, attention has been paid to use of stem cells, and technology for repairing and replacing damaged or defective tissues has been actively studied by using stem cells expanded from donor cells. Most of cells of animals including humans are adherent (scaffold-dependent) cells which cannot survive in a floating state and survive in a state of being adhered to something. For this reason, various developments of functional culture substrates for culturing adherent (scaffold-dependent) cells at high density to obtain cultured tissues similar to living tissues have been conducted.

As a cell culture substrate, plastic (for example: polystyrene) or glass vessels have been conventionally used, and it has been reported that a plasma treatment or the like is performed to a surfaces of these cell vessels. The substrate subjected to the treatment has excellent adhesion to cells, and can be used to grow cells and maintain their function.

Meanwhile, regarding a structure of the cell culture substrate (cell culture vessel), in addition to a conventional flat dish (plate) structure, various structures, such as a structure in which a porous body is inserted as a culture scaffold in a bag, a hollow fiber structure, a sponge structure, a flocculent (glass wool) structure, and a structure in which a plurality of dishes are laminated, have been developed. It is difficult or impossible to perform plasma irradiation to culture vessels having such diversified and complicated structures.

In this regard, a technique using a polymer that has adhesiveness to cells (cellular adhesiveness) and a property to prompt proliferation of cells (cell proliferation activity) has been proposed. For example, Non Patent Literature 1 discloses that a polymer substrate is coated with a homopolymer of methoxyethyl acrylate (PMEA; polymethoxyethyl acrylate) to obtain cellular adhesiveness and cell proliferation activity.

CITATION LIST

Non Patent Literatures

Non Patent Literature 1: Colloids and Surfaces B; Biointerfaces 145 (2016) 586-596.

SUMMARY OF THE INVENTION

The polymer such as polymethoxyethyl acrylate (PMEA) as disclosed in Non Patent Literature 1 can impart cellular adhesiveness and cell proliferation activity to a cell culture substrate. Further, since such a polymer is excellent in coating operability, even in the case of a cell culture substrate having a complicated structure as described above, the polymer can impart cellular adhesiveness and cell proliferation activity.

However, a cell culture substrate (cell culture vessel) having a complicated structure is difficult to coat a polymer such as PMEA with a constant thickness and the polymer such as PMEA also has a problem in that cell proliferation activity is degraded as a thickness of a coating layer increases.

Therefore, the present invention has been made in view of the above-described circumstances, and an object thereof is to provide a means capable of obtaining excellent cell proliferation activity without depending on a thickness of a coating layer in a technique of coating a cell culture substrate (cell culture vessel) using a polymer.

The present inventors have conducted intensive studies to solve the above-described problems. As a result, the present inventors have found that the above-described problems can be solved by coating a surface of a cell culture substrate (polymer substrate) using a copolymer containing a structural unit derived from carboxyalkyl (meth)acrylate having a specific structure and a structural unit derived from an ethylenically unsaturated monomer having a hydroxyl group, at a specific composition (molar ratio). The present invention has been completed on the basis of the above finding.

That is, the object can be achieved by a cell culture substrate (substrate for cell culture) comprising a coating layer on at least one surface of a polymer substrate, wherein the coating layer contains a copolymer comprising more than 40% by mole and less than 100% by mole of a structural unit (1) derived from carboxyalkyl (meth)acrylate represented by the following Formula (1) and more than 0% by mole and less than 60% by mole of a structural unit (2) derived from ethylenically unsaturated monomer having a hydroxyl group (the total of the structural unit (1) and the structural unit (2) is 100% by mole).

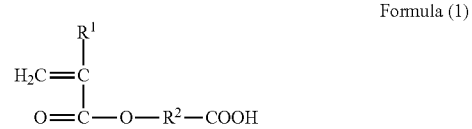

Formula (1)

wherein $R^1$ represents a hydrogen atom or a methyl group and $R^2$ represents an alkylene group having 2 or 3 carbon atoms.

DETAILED DESCRIPTION

Figure 1:
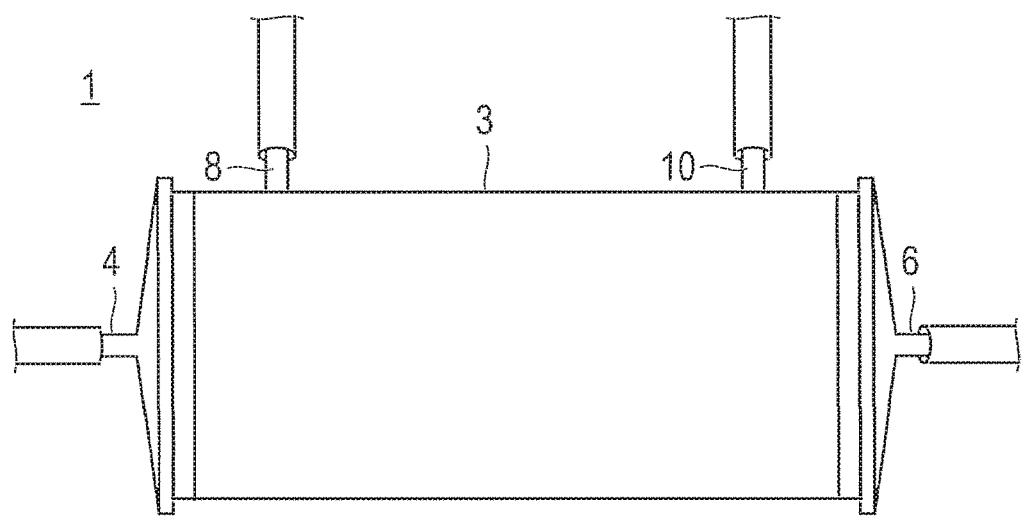
FIG. 1 is a partial side view illustrating an embodiment of a bioreactor (hollow fiber type bioreactor) of the present invention.

A cell culture substrate of the present invention has a coating layer on at least one surface of a polymer substrate, the coating layer includes a copolymer comprising more than 40% by mole and less than 100% by mole of a structural unit (1) derived from carboxyalkyl (meth)acrylate represented by the following Formula (1) and more than 0% by mole and less than 60% by mole of a structural unit (2) derived from ethylenically unsaturated monomer having a hydroxyl group (the total of the structural unit (1) and the structural unit (2) is 100% by mole):

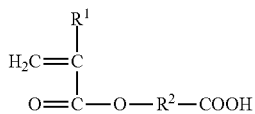

Formula (1)

wherein represents a hydrogen atom or a methyl group and R² represents an alkylene group having 2 or 3 carbon atoms.

By the copolymer according to the present invention, it is possible to provide a means capable of obtaining excellent cell proliferation activity without depending on a thickness of a coating layer in a technique of coating a cell culture substrate (cell culture vessel) using a polymer.

In the present description, the carboxyalkyl (meth)acrylate represented by the Formula (1) is also simply referred to as the "carboxyalkyl (meth)acrylate," and the structural unit derived from carboxyalkyl (meth)acrylate represented by the Formula (1) is also simply referred to as the "structural unit (1)". Further, the ethylenically unsaturated monomer having a hydroxyl group is also simply referred to as the "ethylenically unsaturated monomer," and the structural unit derived from ethylenically unsaturated monomer having a hydroxyl group is also simply referred to as the "structural unit (2)". Furthermore, the copolymer comprising the structural unit (1) and the structural unit (2) is also simply referred to as the "copolymer" or the "copolymer according to the present invention".

Further, in the present description, the term "(meth) acrylate" includes both acrylate and methacrylate". Similarly, the term "(meth)acrylic acid" includes both acrylic acid and methacrylic acid, and "(meth)acryloyl" includes both acryloyl and methacryloyl.

The cell culture substrate of the present invention has a feature in that a coating layer containing the copolymer is formed on at least one surface of the polymer substrate. The coating layer (coating film, coating) formed by using the copolymer has excellent cell proliferation ability (cell expansion ability) even when the film thickness changes. Further, the coating film (coating layer) formed by using the copolymer can maintain favorable cellular adhesiveness even when the film thickness changes. Here, the mechanism for exhibiting the effects by the present invention is presumed to be as follows. Incidentally, the present invention is not limited to the following presumption.

Conventionally, as a means for imparting cell proliferation activity or cellular adhesiveness, there has been a method of applying a cell adhesion factor such as fibronectin, laminin, or collagen to a substrate, a method of subjecting a substrate to treatment with plasma, gamma rays, or electrons, and the like. Of them, the former method has problems in that a cell adhesion factor is expensive and cannot be typically reused since the cell adhesion factor is a natural material, and the like. Further, in the latter method, the plasma treatment can impart particularly excellent cell proliferation activity to a substrate. Meanwhile, in recent years, a structure in which a porous body is inserted as a culture scaffold in a bag, a hollow fiber structure, a sponge structure, a flocculent (glass wool) structure, and a structure in which a plurality of dishes are laminated are used as a suitable culture scaffold. However, the latter method has a problem in that it is difficult or impossible to apply the method to such diversified and complicated structure. Currently, from the viewpoint that those complicated structures are excellent as a culture scaffold, those complicated structures are demanded as a culture scaffold and a means for providing excellent cell proliferation activity with respect to such a culture scaffold is demanded.

In view of the circumstances, the present inventors have focused on the fact that a polymer is excellent in coating operability and have conducted intensive studies on a polymer excellent in cell proliferation activity. It has been conventionally known that polymethoxyethyl acrylate has cell proliferation activity and cellular adhesiveness. However, an ability to expand cells on a substrate (cell expansion ability, cell proliferation activity) of polymethoxyethyl acrylate is degraded as the thickness of the coating film thereof increases (comparison between Comparative Example 2-1 and Comparative Example 2-2 in the following Table 1). Further, the cellular adhesiveness of the coating film of polymethoxyethyl acrylate is degraded as the thickness of the coating film thereof increases (comparison between Comparative Example 2-1 and Comparative Example 2-2 in the following Table 2).

Therefore, the present inventors have evaluated cell proliferation activity and cellular adhesiveness of polymers and copolymers derived from various monomers, and as a result, have first found that a copolymer of carboxyalkyl (meth) acrylate and an ethylenically unsaturated monomer having a hydroxyl group has little film thickness dependence of cell proliferation activity (cell expansion ability). Further, the present inventors have also found that these copolymers have little film thickness dependence of cellular adhesiveness.

The detailed mechanism thereof is not clear but is presumed that the hardness of the coating layer (coating film) is involved. Specifically, the cell proliferation activity (cell expansion ability) and the cellular adhesiveness are dependent on the hardness of the surface of a culture scaffold to which the cells adhere, and the cell proliferation activity (cell expansion ability) and the cellular adhesiveness are considered to be improved when the surface of the culture scaffold has moderate hardness. That is, it is presumed that, in a case where the surface of a cell scaffold is too hard or too soft, the cell proliferation activity (cell expansion ability) and the cellular adhesiveness are degraded.

Herein, in a case where the thickness of the coating layer (culture scaffold) to which cells adhere is small, the hardness of the components forming the coating layer has an insignificant effect on the hardness of the surface of the coating layer. Therefore, in such a case, the hardness of the surface of the coating layer is not dependent on the hardness of the components forming the coating layer and a certain degree of cell proliferation activity can be exhibited (Examples 1-2 to 4-2 and Comparative Examples 1-2 to 4-2 in the following Table 1). On the other hand, in a case where the thickness of the coating layer is large, the hardness of the surface of the coating layer (culture scaffold) is greatly dependent on the hardness of the components forming the coating layer. Therefore, when a coating layer having a large thickness is formed using a soft component such as polymethoxyethyl acrylate, the surface of the coating layer (culture scaffold) to which cells adhere is in a state of being too soft, and cell proliferation activity is degraded (comparison between Comparative Example 2-1 and Comparative Example 2-2 in the following Table 1). As a result, it is considered that cell proliferation activity changes depending on the thickness of the coating layer.

On the other hand, since the copolymer according to the present invention has moderate hardness, even in a case where the thickness of the coating layer increases, the surface of the coating layer (culture scaffold) to which cells adhere can maintain a moderately hard state. Thus, similarly to a case where the thickness is small, favorable cell proliferation activity (cell expansion ability) can be maintained. That is, it is considered that since the copolymer according to the present invention has moderate hardness, the film thickness dependence of the cell proliferation activity (cell expansion ability) is small. Further, similarly, even in a case where the thickness of the coating layer increase, the surface of the coating layer (culture scaffold) to which cells adhere has a moderately hard state so that the coating layer is also excellent in cellular adhesiveness.

In addition, a carboxyl group (—COOH) of carboxyalkyl (meth)acrylate forming the structural unit (1) and a hydroxyl group (—OH) of ethylenically unsaturated monomer having a hydroxyl group which forms the structural unit (2) are presumed to promote expansion (proliferation) or adhesion of cells via activation or induction of signal of cell-expansion (proliferation) or cell-adhesion. Herein, since the copolymer according to the present invention contains the structural unit (1) and the structural unit (2) at a specific composition (molar ratio), a carboxyl group and a hydroxyl group are contained at a proper ratio. Therefore, it is considered that the effect of promoting expansion (proliferation) or adhesion of cells of a coating film formed by the copolymer according to the present invention is high. Thus, also from this point, the cell culture substrate according to the present invention has excellent cell proliferation activity (cell expansion ability). Further, similarly, the copolymer according to the present invention also has favorable cellular adhesiveness since functional groups (a carboxyl group and a hydroxyl group) involved in activation or induction of signals of adhesion of cells are contained with proper balance. Incidentally, for example, a homopolymer of hydroxyalkyl (meth)acrylate lowers cell adhesion. In view of this point, the finding of the present inventors that the copolymer of carboxyalkyl (meth)acrylate and an ethylenically unsaturated monomer having a hydroxyl group can improve cellular adhesiveness as well as cell proliferation activity (cell expansion ability) as compared to a homopolymer of each monomer.

Hereinafter, a preferred embodiment of the present invention will be described. Incidentally, the present invention is not limited only to the following embodiment.

In the present description, the term "X to Y" which indicates a range means the term "X or more and Y or less" including X and Y. Further, unless otherwise specified, operations and measurements of physical properties and the like are conducted under conditions of room temperature (20 to 25° C.)/relative humidity of 40 to 50% RH.

<Cell Culture Substrate>

The cell culture substrate of the present invention comprises a coating layer containing the copolymer is formed on at least one surface of a polymer substrate. The copolymer according to the present invention has favorable cell proliferation activity (cell expansion ability) even when the film thickness changes. Further, the copolymer according to the present invention can maintain favorable cellular adhesiveness even when the film thickness changes. In addition, the coating layer can be simply formed in such a manner that the copolymer is dissolved in a solvent and the resultant solution is applied to a surface of the polymer substrate. Therefore, by using the copolymer according to the present invention, a coating layer (cell proliferation layer) having cell proliferation activity (and further cellular adhesiveness) can be formed on a surface of cell culture substrate (cell culture vessel) regardless of the shape or design. At this time, since the copolymer according to the present invention exhibits favorable cell proliferation activity (and further cellular adhesiveness) even when the film thickness changes, certain cell proliferation activity (and further cellular adhesiveness) can be imparted to a cell culture substrate (cell culture vessel) having a complicated structure that is difficult to coat a polymer (copolymer) with a constant thickness.

[Copolymer]

The copolymer according to the present invention has more than 40% by mole and less than 100% by mole of a structural unit (1) derived from carboxyalkyl (meth)acrylate represented by Formula (1) and more than 0% by mole and less than 60% by mole of a structural unit (2) derived from ethylenically unsaturated monomer having a hydroxyl group. Herein, the total of the structural unit (1) and the structural unit (2) is 100% by mole.

The copolymer has the structural unit (1), the structural unit (2), and as necessary, a structural unit derived from another monomer which will be described later in detail. Here, the arrangement of each structural unit is not particularly limited, but may be in the form of block (block copolymer), random (random copolymer), or alternate (alternate copolymer).

It is presumed that a carboxyl group of the carboxyalkyl (meth)acrylate (structural unit (1)) and a hydroxyl group of the ethylenically unsaturated monomer (structural unit (2)) having a hydroxyl group impart cell proliferation activity (cell expansion ability) to a substrate, respectively. Since the copolymer according to the present invention contains the structural unit (1) and the structural unit (2) at a specific composition (molar ratio), the balance between the carboxyl group and the hydroxyl group is properly adjusted, and the effect of expanding cells (cell proliferation activity) as described above is improved.

On the other hand, a (co)polymer containing the structural unit (2) in a large ratio tends to become easily hard. Therefore, regarding a coating layer (coating film) formed by a polymer containing only the structural unit (2), it is considered that when the thickness thereof is large, the polymer forming the coating layer (coating film) is too hard, so that cell proliferation activity (cell expansion ability) is degraded. That is, it is considered that if the coating layer (coating film) is too hard, cells are difficult to partially enter into the coating layer (coating film) when the cells stretch, so that cell proliferation activity (cell expansion ability) is degraded.

Further, a (co)polymer containing the structural unit (1) in a large ratio tends to become easily soft. Therefore, regarding a coating layer (coating film) formed by a polymer containing only the structural unit (1), it is considered that when the thickness thereof is large, the coating layer (coating film) is too soft, so that cell proliferation activity (cell expansion ability) is degraded. That is, it is considered that if the coating layer (coating film) is too soft, cells are difficult to stably hold with respect to the coating layer (coating film) (cells cannot use the coating layer (coating film) as a scaffold, so that the cells are difficult to proliferously grow (expand) along the surface of the coating layer (coating film) or cannot be proliferously grown (expanded). As a result, it is considered that cell proliferation activity (cell expansion ability) is degraded.

On the other hand, by combining the structural unit (1) with the structural unit (2) at a specific composition (molar ratio), a copolymer having moderate hardness can be obtained. As a result, regarding a coating layer (coating film) using a copolymer containing the structural unit (1) and the structural unit (2) at a specific composition (molar ratio), even in a case where the thickness thereof is large, the surface of the coating layer (coating film) is in a state of having moderate hardness. As a result, it is considered that the film thickness dependence of the cell proliferation activity can be reduced without the cell proliferation activity being degraded. In addition thereto, by applying a solution of the copolymer to a surface of a polymer substrate, a coating layer can be simply formed on a substrate having various shapes. Therefore, by using the copolymer according to the present invention, a coating layer (cell adhesion layer) having excellent in cell proliferation activity (and further cellular adhesiveness) can be formed with on a cell culture substrate (cell culture vessel) having various shapes or designs.

The structural unit (1) constituting the copolymer according to the present invention is contained at a ratio of more than 40% by mole and less than 100% by mole with respect to the total (100% by mole) of the structural unit (1) and the structural unit (2), and the structural unit (2) is contained at a ratio of more than 0% by mole and less than 60% by mole with respect to the total (100% by mole) of the structural unit (1) and the structural unit (2). Here, when the composition of the structural unit (1) is 40% by mole or less, the effects of the carboxyalkyl (meth)acrylate (structural unit (1)) (cell proliferation activity promoting effect, and further cellular adhesiveness imparting effect) cannot be exhibited. Specifically, when the composition of the structural unit (1) is 40% by mole or less, a copolymer having moderate hardness cannot be obtained (a copolymer having excessive hardness is obtained), and in a case where a coating layer (coating film) having a large thickness and a coating layer (coating film) having a small thickness are formed using such a copolymer, a certain degree of cell proliferation activity is not obtainable (comparison between Comparative Example 1-1 and Comparative Example 1-2 in the following Table 1). Further, similarly, cellular adhesiveness is also degraded. On the other hand, when the composition of the structural unit (1) is 100% by mole, in a case where a coating layer (coating film) having a large thickness is formed, the coating layer (coating film) is too soft, so that the effect obtained by forming a coating layer (coating film) (cell proliferation activity imparting effect) cannot be exhibited and only the same degree of cell proliferation activity as in a non-treated cell culture substrate (cell culture vessel) can be exhibited (comparison among Comparative Example 4-1, Comparative Example 4-2, and Reference Example 1 in the following Table 1).

From the viewpoint of further improvement in cell proliferation activity (and further cellular adhesiveness), and the like, it is preferable that the structural unit (1) is contained at a ratio of 45% by mole or more and 98% by mole or less with respect to the total of the structural unit (1) and the structural unit (2), and the structural unit (2) is contained at a ratio of 2% by mole or more and 55% by mole or less with respect to the total of the structural unit (1) and the structural unit (2). It is more preferable that the structural unit (1) is contained at a ratio of 55% by mole or more and 95% by mole or less with respect to the total of the structural unit (1) and the structural unit (2), and the structural unit (2) contained at a ratio of is 5% by mole or more and 45% by mole or less with respect to the total of the structural unit (1) and the structural unit (2). Furthermore, from the viewpoint of obtaining a copolymer that can reduce the film thickness dependence of the cellular adhesiveness in addition to cell proliferation activity, it is more preferable that the structural unit (1) contained at a ratio of is 60% by mole or more and 90% by mole or less with respect to the total of the structural unit (1) and the structural unit (2), and the structural unit (2) contained at a ratio of is 10% by mole or more and 40% by mole or less with respect to the total of the structural unit (1) and the structural unit (2). Furthermore, particularly from the viewpoint of being excellent in cell proliferation activity, it is particularly preferable that the structural unit (1) is contained at a ratio of 65% by mole or more and 90% by mole or less with respect to the total of the structural unit (1) and the structural unit (2), and the structural unit (2) contained at a ratio of is 10% by mole or more and 35% by mole or less with respect to the total of the structural unit (1) and the structural unit (2). It is most preferable that the structural unit (1) is 7 contained at a ratio of 5% by mole or more and 85% by mole or less with respect to the total of the structural unit (1) and the structural unit (2), and the structural unit (2) contained at a ratio of is 15% by mole or more and 25% by mole or less with respect to the total of the structural unit (1) and the structural unit (2).

That is, according to the preferred embodiment of the present invention, the copolymer is a copolymer having 45% by mole or more and 98% by mole or less of the structural unit (1) and 2% by mole or more and 55% by mole or less of the structural unit (2) (the total of the structural unit (1) and the structural unit (2) is 100% by mole). Further, according to the more preferred embodiment of the present invention, the copolymer is a copolymer having 55% by mole or more and 95% by mole or less of the structural unit (1) and 5% by mole or more and 45% by mole or less of the structural unit (2) (the total of the structural unit (1) and the structural unit (2) is 100% by mole). Furthermore, from the viewpoint of obtaining a copolymer that can reduce the film thickness dependence of the cellular adhesiveness in addition to cell proliferation activity, according to the further more preferred embodiment of the present invention, the copolymer is a copolymer having 60% by mole or more and 90% by mole or less of the structural unit (1) and 10% by mole or more and 40% by mole or less of the structural unit (2) (the total of the structural unit (1) and the structural unit (2) is 100% by mole). Furthermore, particularly from the viewpoint that the film thickness dependence of the cell proliferation activity is small, according to the particularly preferred embodiment of the present invention, the copolymer is a copolymer having 65% by mole or more and 90% by mole or less of the structural unit (1) and 10% by mole or more and 35% by mole or less of the structural unit (2) (the total of the structural unit (1) and the structural unit (2) is 100% by mole). Furthermore, according to the most preferred embodiment of the present invention, the copolymer is a copolymer having 75% by mole or more and 85% by mole or less of the structural unit (1) and 15% by mole or more and 25% by mole or less of the structural unit (2) (the total of the structural unit (1) and the structural unit (2) is 100% by mole).

The copolymer according to the present invention essentially includes the structural unit (1) and the structural unit (2), but may further have a structural unit derived from another monomer in addition to the structural unit (1) and the structural unit (2). Here, another monomer is not particularly limited as long as it does not inhibit desired characteristics (cell proliferation activity and/or cellular adhesiveness). Specific examples of the another monomer include acrylamide, N,N-dimethylacrylamide, N,N-diethylacrylamide, methacrylamide, N,N-dimethylmethacrylamide, N,N-diethylmethacrylamide, ethylene, propylene, N-vinylacetamide, N-isopropenyl acetamide, N-(meth)acryloyl morpholine, and the like. These other monomers may be used singly or in combination of two or more kinds thereof. A composition of the structural unit derived from another monomer in a case where the copolymer further has a structural unit derived from another monomer is not particularly limited as long as it does not inhibit desired characteristics (cell proliferation activity and cellular adhesiveness), but the composition of the structural unit derived from another monomer is preferably more than 0% by mole and less than 10% by mole and more preferably about 3 to 8% by mole with respect to the total of the structural unit (1) and the structural unit (2).

For the purpose of improving cell proliferation activity (and further cellular adhesiveness), it is preferable that the copolymer includes no structural units derived from another monomer, that is, the copolymer according to the present invention is formed only of the structural unit (1) and the structural unit (2). That is, according to the preferred embodiment of the present invention, the copolymer is composed of the structural unit (1) and the structural unit (2).

Therefore, according to the more preferred embodiment of the present invention, the copolymer is a copolymer which is composed of 60% by mole or more and 90% by mole or less of the structural unit (1) and 10% by mole or more and 40% by mole or less of the structural unit (2) (the total of the structural unit (1) and the structural unit (2) is 100% by mole). With such a composition (molar ratio), in addition to cell proliferation activity, the film thickness dependence of the cellular adhesiveness can also be reduced. Further, according to the further more preferred embodiment of the present invention, the copolymer is a copolymer which is composed of 65% by mole or more and 90% by mole or less of the structural unit (1) and 10% by mole or more and 35% by mole or less of the structural unit (2) (the total of the structural unit (1) and the structural unit (2) is 100% by mole). With such a composition (molar ratio), particularly, the film thickness dependence of the cell proliferation activity is small. Further, according to the particularly preferred embodiment of the present invention, the copolymer is a copolymer configured by 75% by mole or more and 85% by mole or less of the structural unit (1) and 15% by mole or more and 25% by mole or less of the structural unit (2) (the total of the structural unit (1) and the structural unit (2) is 100% by mole).

The structural unit (1) is derived from carboxyalkyl (meth)acrylate of the following Formula (1). Incidentally, the structural unit (1) constituting the copolymer may be used singly or in combination of two or more kinds thereof. That is, the structural unit (1) may be composed only one kind of the structural unit derived from carboxyalkyl (meth)acrylate of the following Formula (1) or may be composed of two or more kinds of the structural units derived from carboxyalkyl (meth)acrylate of the following Formula (1). In the latter case, each structural unit may be present in the form of block or random. Further, when the structural unit (1) is composed of two or more kinds of the structural units derived from carboxyalkyl (meth)acrylate of the following Formula (1), a composition of the structural unit (1) is a total ratio (molar ratio (% by mole)) of the structural units derived from carboxyalkyl (meth)acrylate with respect to the total of the structural unit (1) and the structural unit (2).

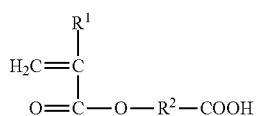

Formula (1)

In the Formula (1), $R^1$ is a hydrogen atom or a methyl group. $R^2$ is an alkylene group having 2 or 3 carbon atoms. The alkylene group having 2 or 3 carbon atoms includes an ethylene group ($-CH_2CH_2-$), a trimethylene group ($-CH_2CH_2CH_2-$), and a propylene group ($-CH(CH_3)CH_2-$ or $-CH_2CH(CH_3)-$). Among these, from the viewpoint of further improvement in cell proliferation activity (and further cellular adhesiveness), or the like, $R^2$ preferably represents an ethylene group ($-CH_2CH_2-$) or a trimethylene group ($-CH_2CH_2CH_2-$), and more preferably an ethylene group ($-CH_2CH_2-$).

Specifically, examples of the carboxyalkyl (meth)acrylate include carboxyethyl acrylate, carboxypropyl acrylate, carboxyisopropyl acrylate, carboxyethyl methacrylate, carboxy propyl methacrylate, carboxyisopropyl methacrylate, and the like. These may be used singly or in combination of two or more kinds thereof. Among these, from the viewpoint of further improvement in cell proliferation activity (and further cellular adhesiveness), and the like, carboxyethyl (meth)acrylate is preferred and carboxyethyl acrylate (CEA) is more preferred.

The structural unit (2) is derived from an ethylenically unsaturated monomer having a hydroxyl group. The structural unit (2) constituting the copolymer may be used singly or in combination of two or more kinds thereof. That is, the structural unit (2) may be composed only one kind of the structural unit derived from ethylenically unsaturated monomer having a hydroxyl group or may be composed of two or more kinds of the structural units derived from ethylenically unsaturated monomer having a hydroxyl group. In the latter case, each structural unit may be present in the form of block or random. Further, when the structural unit (2) is composed of two or more kinds of the structural units derived from ethylenically unsaturated monomer having a hydroxyl group, a composition of the structural unit (2) is a total ratio (molar ratio (% by mole)) of the structural units derived from ethylenically unsaturated monomer having a hydroxyl group with respect to the total of the structural unit (1) and the structural unit (2).

The ethylenically unsaturated monomer having a hydroxyl group which forms the structural unit (2) is not particularly limited as long as it is a compound having one or more hydroxyl groups ($-OH$) and one or more ethylenically unsaturated groups in one molecule. Herein, the "ethylenically unsaturated group" refers to a group in which a hydrogen atom of ethylene ($CH_2=CH_2$) is substituted, and examples thereof include a (meth)acryloyl group, a vinyl group, an allyl group, a vinyl ether group, and the like. Incidentally, only one of these groups may be contained in one molecule of the ethylenically unsaturated monomer or two or more groups may be contained.

Of them, as the ethylenically unsaturated group, a (meth)acryloyl group is preferred. That is, according to the preferred embodiment of the present invention, the ethylenically unsaturated monomer has a (meth)acryloyl group. Thus, the ethylenically unsaturated monomer is preferably a compound having one or more hydroxyl groups and one or more acryloyl groups or methacryloyl groups in one molecule. The upper limit of the number of hydroxyl groups and (meth)acryloyl groups contained in the ethylenically unsaturated monomer is not particularly limited, but from the viewpoint of controllability of cell proliferation activity (cell expansion ability) and cellular adhesiveness, the number of hydroxyl groups in one molecule is preferably 3 or less, more preferably 2 or less, and particularly preferably 1. Further, from the viewpoint of the ease of preparation of the copolymer with carboxyalkyl (meth)acrylate represented by the Formula (1), controllability of the composition (molar ratio) of each structural unit, and controllability of cell proliferation activity (cell expansion ability) and cellular adhesiveness, the number of (meth)acryloyl groups in one molecule is preferably 3 or less and more preferably 2 or less. In particular, from the viewpoint of controlling the composition (molar ratio) of each structural unit to further reduce the film thickness dependence of cell proliferation activity (and further cellular adhesiveness), the number of (meth)acryloyl groups in one molecule is particularly preferably 1.

According to the preferred embodiment of the present invention, the structural unit (2) is derived from hydroxyalkyl (meth)acrylate represented by the following Formula (2). That is, the ethylenically unsaturated monomer is preferably hydroxyalkyl (meth)acrylate represented by the following Formula (2). The structural unit (2) constituting the copolymer may be used singly or in combination of two or more kinds thereof. That is, the structural unit (2) may be composed only one kind of the structural unit derived from hydroxyalkyl (meth)acrylate represented by the following Formula (2), or may be composed of two or more kinds of the structural units derived from hydroxyalkyl (meth)acrylate represented by the following Formula (2). In the latter case, each structural unit may be present in the form of block or random. Further, when the structural unit (2) is composed of two or more kinds of the structural units derived from hydroxyalkyl (meth)acrylate represented by the following Formula (2), a composition of the structural unit (2) is a total ratio (molar ratio (% by mole)) of the structural units derived from hydroxyalkyl (meth)acrylate with respect to the total of the structural unit (1) and the structural unit (2).

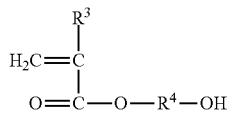

Formula (2)

In the above Formula (2), $R^3$ is a hydrogen atom or a methyl group. $R^4$ is an alkylene group having 2 or 3 carbon atoms. The alkylene group having 2 or 3 carbon atoms includes an ethylene group (—$CH_2CH_2$—), a trimethylene group (—$CH_2CH_2CH_2$—), and a propylene group (—CH($CH_3$)$CH_2$— or —$CH_2CH(CH_3)$—). Among these, from the viewpoint of further improvement in cell proliferation activity (and further cellular adhesiveness), and the like, $R^4$ preferably represents an ethylene group (—$CH_2CH_2$—) or a trimethylene group (—$CH_2CH_2CH_2$—), and more preferably an ethylene group (—$CH_2CH_2$—).

Specifically, examples of hydroxyalkyl (meth)acrylate include hydroxyethyl acrylate, hydroxypropyl acrylate, hydroxyisopropyl acrylate, hydroxyethyl methacrylate, hydroxypropyl methacrylate, hydroxyisopropyl methacrylate, and the like. These may be used singly or in combination of two or more kinds thereof. Among these, from the viewpoint of further improvement in cell proliferation activity (and further cellular adhesiveness), and the like, hydroxyalkyl (meth)acrylate is preferably hydroxyethyl (meth)acrylate and more preferably hydroxyethyl methacrylate (HEMA).

A weight average molecular weight (Mw) of the copolymer is not particularly limited, and is preferably 20,000 to 1,000,000. Within the above range, the solubility of the copolymer in a solvent is can be improved and application to a substrate can be uniformly conducted with ease. From the viewpoint of improving coating film formability, the weight average molecular weight of the copolymer is more preferably 100,000 to 500,000.

In the present description, as the "weight average molecular weight (Mw)," a value measured by gel permeation chromatography (GPC) using polystyrene as a standard and tetrahydrofuran (THF) as a mobile phase respectively is adopted. Specifically, the copolymer is dissolved in tetrahydrofuran (THF) so as to have a concentration of 10 mg/ml, thereby preparing a sample. Regarding the sample prepared as above, GPC column LF-804 (manufactured by Showa Denko K.K.) is attached to a GPC system LC-20 (manufactured by SHIMADZU CORPORATION), THF is supplied as a mobile phase, and polystyrene is used as a standard, to measure GPC of the copolymer. After preparing a calibration curve with polystyrene as standards, the weight average molecular weight (Mw) of the copolymer is calculated on the basis of the curve.

The copolymer according to the present invention can be produced by employing a conventionally known polymerization method such as bulk polymerization, suspension polymerization, emulsion polymerization, solution polymerization, living radical polymerization method, polymerization method using a macroinitiator, polycondensation method, or the like, for example, although not particularly limited thereto. Specifically, in a case where the copolymer according to the present invention is a block copolymer, for example, a living radical polymerization method or a polymerization method using a macroinitiator is preferably used. As the living radical polymerization method, although not particularly limited thereto, a method described in JP H11-263819 A, JP 2002-145971 A, JP 2006-316169 A, or the like, an atom transfer radical polymerization (ATRP) method, and the like can be applied similarly or appropriately modified, for example.

Alternatively, for example, in a case where the copolymer according to the present invention is a random copolymer, it is preferable to use a method of stirring the carboxyalkyl (meth)acrylate of the Formula (1), the ethylenically unsaturated monomer having a hydroxyl group (preferably, the hydroxyalkyl (meth)acrylate of the Formula (2)), and as necessary, one or two or more kinds of monomer which is copolymerizable with those components (another monomer, copolymerizable monomer; the same applies hereinafter), in a polymerization solvent, with a polymerization initiator to prepare a monomer solution, and heating the monomer solution to perform copolymerization. In the method, a polymerization solvent which can be used in the preparation of the monomer solution is not particularly limited as long as it can dissolve the monomer used above. Examples thereof include aqueous solvents such as water, alcohols such as methanol, ethanol, propanol, and isopropanol, and polyethylene glycols; aromatic solvents such as toluene, xylene, and tetralin; halogen-based solvents such as chloroform, dichloroethane, chlorobenzene, dichlorobenzene, and trichlorobenzene; and the like. Among these, taking in consideration of easy dissolution of the monomer, or the like, ethanol is preferable. Further, a concentration of the monomer in the monomer solution is not particularly limited, but the concentration of the monomer in the monomer solution is typically 15 to 60% by weight, more preferably 20 to 50% by weight, and particularly preferably 25 to 45% by weight. Incidentally, the concentration of the monomer means a total concentration of the carboxyalkyl (meth) acrylate of the Formula (1), the ethylenically unsaturated monomer having a hydroxyl group (preferably, the hydroxyalkyl (meth)acrylate of the Formula (2)), and if being used, a monomer which is copolymerizable with those components (another monomer, copolymerizable monomer).

The polymerization initiator is not particularly limited, and a known polymerization initiator may be used. From the viewpoint of high polymerization stability, the polymerization initiator is preferably a radical polymerization initiator. Specific examples thereof include persulfates such as potassium persulfate (KPS), sodium persulfate, and ammonium persulfate; peroxides such as hydrogen peroxide, t-butyl peroxide, and methyl ethyl ketone peroxide; and azo compounds such as azobisisobutyronitrile (AIBN), 2,2'-azobis (4-methoxy-2,4-dimethylvaleronitrile), 2,2'-azobis(2,4-dimethylvaleronitrile), 2,2'-azobis[2-(2-imidazoline-2-yl) propane]dihydrochloride, 2,2'-azobis[2-(2-imidazoline-2-yl)propane]disulfate dihydrate, 2,2'-azobis(2-methylpropionamidine)dihydrochloride, 2,2'-azobis[N-(2-carboxyethyl)-2-methylpropionamidine)]hydrate, 3-hydroxy-1,1-dimethylbutyl peroxyneodecanoate, α-cumylperoxy neodecanoate, 1,1,3,3-tetrabutyl peroxyneodecanoate, t-butyl peroxyneodecanoate, t-butyl peroxyneoheptanoate, t-butyl peroxypivalate, t-amyl peroxyneodecanoate, t-amyl peroxypivalate, di(2-ethylhexyl)peroxydicarbonate, di(secondary butyl)peroxydicarbonate, and azobiscyanovaleric acid. Further, for example, a reducing agent such as sodium sulfite, sodium hydrogen sulfite, or ascorbic acid may be used in combination with the radical polymerization initiator as a redox type initiator. A blending amount of the polymerization initiator is preferably 0.0005 to 0.005 mol with respect to 1 mol of a total amount of the monomers. With such a blending amount of the polymerization initiator, copolymerization of the respective monomers can efficiently proceed.

The polymerization initiator as it is may be mixed with the carboxyalkyl (meth)acrylate of the Formula (1), the ethylenically unsaturated monomer having a hydroxyl group (preferably, the hydroxyalkyl (meth)acrylate of the Formula (2), and if being used, a monomer which is copolymerizable with those components (another monomer, copolymerizable monomer), and a polymerization solvent, or alternatively a solution of the polymerization initiator obtained by being dissolved in another solvent in advance may be mixed with the monomers and the polymerization solvent. In the latter case, another solvent used to dissolve the polymerization initiator is not particularly limited as long as it can dissolve the polymerization initiator, but the same solvent as the polymerization solvent described above can be exemplified. Further, another solvent may be the same as or different from the polymerization solvent, but in consideration of easy control of polymerization, and the like, the same solvent as the polymerization solvent is preferably used. Further, in this case, a concentration of the polymerization initiator in another solvent is not particularly limited, but in consideration of easy mixing, and the like, the addition amount of the polymerization initiator is preferably 0.1 to 10 parts by weight and more preferably 0.5 to 5 parts by weight, with respect to 100 parts by weight of another solvent.

Further, in the case of using the polymerization initiator in the solution state, deaeration treatment may be performed in advance before adding a solution in which the monomers (carboxyalkyl (meth)acrylate, ethylenically unsaturated monomer having a hydroxyl group, and a copolymerizable monomer which is used optionally) are dissolved in the polymerization solvent, to the polymerization initiator solution. For the deaeration treatment, for example, the solution may be bubbled with an inert gas such as nitrogen gas or argon gas for about 0.5 to 5 hours. In the deaeration treatment, the solution may be adjusted to about 30° C. to 80° C., preferably to a polymerization temperature in a polymerization step as described below.

Next, the monomer solution is heated to copolymerize the respective monomers. Here, as the copolymerization method, for example, a known polymerization method such as radical polymerization, anionic polymerization, or cationic polymerization can be adopted, and radical polymerization which facilitates production is preferably used.

The polymerization conditions are not particularly limited as long as the carboxyalkyl (meth)acrylate of the Formula (1), the ethylenically unsaturated monomer having a hydroxyl group (preferably, the hydroxyalkyl (meth)acrylate of the Formula (2)), and if being used, a monomer which is copolymerizable with those components (another monomer, copolymerizable monomer)) can be copolymerized. Specifically, the copolymerization temperature is preferably 30 to 80° C. and more preferably 40° C. to 55° C. Further, the copolymerization time is preferably is 1 to 24 hours and more preferably 5 to 12 hours. Under such conditions, copolymerization of the respective monomers can efficiently proceed. Further, it is possible to effectively suppress or prevent gelation in the polymerization step and to achieve high production efficiency.

As necessary, a chain transfer agent, a polymerization rate-adjusting agent, a surfactant, and other additives may be appropriately used during the polymerization.

An atmosphere under which the polymerization reaction is carried out is not particularly limited, and the reaction can be carried out under an air atmosphere, an inert gas atmosphere such as nitrogen gas or argon gas, and the like. Further, during the polymerization reaction, the reaction solution may be stirred.

The polymer after polymerization can be purified by a general purification method such as a reprecipitation method (precipitation method), a dialysis method, an ultrafiltration method, or an extraction method.

The purified polymer can be dried by an arbitrary method such as freeze drying, vacuum drying, spray drying, or heat drying, but freeze drying or vacuum drying is preferred from the viewpoint that the physical properties of the polymer are less affected.

[Polymer Substrate]

In the present invention, a coating layer containing the copolymer is formed on at least one surface of the polymer substrate. Herein, the coating layer is formed on at least a surface of the polymer substrate with which cells contact (for example, on which a liquid containing cells flows or cells are cultured). Further, it is not necessary to form the coating layer on an entire surface of the polymer substrate. The coating layer may be formed on a portion (a part) of the surface of the polymer substrate with which cells contact (for example, on which a liquid containing cells flows or cells are cultured). From the viewpoint of further improving cell proliferation activity (and further cellular adhesiveness), the coating layer is preferably formed on the entire surface of the polymer substrate at the side with which cells contact (for example, on which a liquid containing cells flows or cells are cultured).

Herein, a structure of the polymer substrate is not limited. In addition to the plane structure, the polymer substrate can be designed in various structures (forms) such as a structure in which a porous body is inserted, a hollow fiber structure, a porous membrane structure, a sponge structure, a flocculent (glass wool) structure. As described later, the cell culture substrate of the present invention can be suitably used in a bioreactor, particularly, a hollow fiber type bioreactor. Therefore, the polymer substrate preferably has hollow fibers and is more preferably a porous membrane formed of a plurality of hollow fibers. That is, according to the preferred embodiment of the present invention, the polymer substrate is a porous membrane. In the case where the polymer substrate is a porous membrane, an inner diameter (diameter) of the hollow fiber constituting the porous membrane is not particularly limited, but is preferably 50 to 1,000 µm, more preferably 100 to 500 µm, and particularly preferably about 150 to 350 µm. An outer diameter (diameter) of the hollow fiber constituting the porous membrane is not particularly limited, but is preferably 100 to 1,200 µm, more preferably 150 to 700 µm, and particularly preferably about 200 to 500 µm. A length of the hollow fiber constituting the porous membrane when the polymer substrate is a porous membrane is not particularly limited, but is preferably 50 to 900 mm, more preferably 100 to 700 mm, and particularly preferably about 150 to 500 mm. The number of the hollow fibers constituting the porous membrane when the polymer substrate is a porous membrane is not particularly limited, but is, for example, about 1,000 to 100,000, more preferably 3,000 to 50,000, and particularly preferably about 5,000 to 25,000. In an embodiment, the polymer substrate is configured by about 9,000 hollow fibers having an average length of about 295 mm, an average inner diameter of 215 µm, and an average outer diameter of 315 µm. Herein, the coating layer may be formed on the inner side or the outer side of the hollow fiber membrane, but is preferably formed on the inner (lumen) surface.

A method for producing a hollow fiber and a porous membrane is not particularly limited, and a known production method can be applied similarly or appropriately modified. For example, it is preferable that micro fine holes are formed on a wall of hollow fiber by a stretching method or a solid-liquid phase separation method.

A material constituting the polymer substrate is also not particularly limited. Specific examples thereof include a polyolefin resin such as polypropylene or polyethylene, a hydrophobic polymer material such as polystyrene, polysulfone, polyacrylonitrile, polytetrafluoroethylene, or cellulose acetate, and the like. Further, the polymer substrate may be produced by a semi-permeable, biocompatible polymer material such as a blend of polyamide, polyarylethersulfone, and polyvinylpyrrolidone (PA/PAES/PVP). Such a semi-permeable membrane allows transfer of nutrient, waste, and dissolved gas through the membrane between the extracapillary (EC) space of the hollow fiber and the intracapillary (IC) space of the hollow fiber. The molecule transfer characteristics of the hollow fiber membrane may be selected such that a metabolic waste product can pass through the membrane to be dispersed into a hollow fiber lumen and then removed therefrom, and at the same time, loss of an expensive reagent (such as a growth factor or cytokine) necessary for cell growth from the hollow fiber can be minimized. In a case where the polymer substrate is hollow fibers formed of PA/PAES/PVP, an outer layer of the hollow fiber may have an open pore structure with a certain surface roughness. An opening (diameter) of the pore is not particularly limited, but is in the range of about 0.5 to about 3 µm, and the number of pores on the outer surface of the hollow fiber may be in the range of about 10,000 to about 150,000 per 1 square millimeter (1 $mm^2$). A thickness of the outer layer of the hollow fiber is not particularly limited, and for example, is in the range of about 1 to about 10 µm. The hollow fiber may have an additional layer (second layer) on the outer side, and at this time, the additional layer (second layer) preferably has a sponge structure having a thickness of about 1 to about 15 µm. The second layer having such a structure can serve as a support for the outer layer. Further, in this embodiment, the hollow fiber may have a further additional layer (third layer) at the outer side of the second layer. In this embodiment, the further additional layer (third layer) preferably has a finger-like structure. With the third layer having such a structure, mechanical stability is obtainable. Further, a high void volume with low resistance to membrane transfer of molecules can be provided. In this embodiment, during use, the finger-like voids are filled with a fluid and the fluid lowers resistance for diffusion and convection as compared with a matrix with a sponge-filled structure having a lower void volume. This third layer has a thickness of, preferably, about 20 to about 60 µm.

Further, the polymer substrate may have about 65% by weight to about 95% by weight of at least a hydrophobic polymer and about 5% by weight to about 35% by weight of at least a hydrophilic polymer. At this time, a total amount of the hydrophobic polymer and the hydrophilic polymer is 100% by weight. Here, the hydrophobic polymer is not particularly limited, and examples thereof include polyamide (PA), polyaramide (PAA), polyarylethersulfone (PAES), polyethersulphone (PES), polysulfone (PSU), polyarylsulphone (PASU), polycarbonate (PC), polyether, polyurethane (PUR), polyetherimide, and polyethersulphone; a mixture of polyarylethersulfone and polyamide; and the like. These hydrophobic polymers may be used singly or as a mixture of two or more kinds thereof. Further, the hydrophilic polymer is not particularly limited, and examples thereof include polyvinylpyrrolidone (PVP), polyethylene glycol (PEG), polyglycolmonoester, water soluble cellulosic derivatives, polysorbate, polyethylene-polypropylene oxide copolymers, and the like. These hydrophilic polymers may be used singly or as a mixture of two or more kinds thereof.

A method of forming a coating layer containing the copolymer according to the present invention on a surface of the polymer substrate is not particularly limited. For example, in a case where the surface of the polymer substrate has a flat dish (plate) structure, a method of applying a copolymer-containing solution obtained by dissolving the copolymer according to the present invention to a predetermined surface (for example, by adding to a well) and then drying coating film can be used. Further, for example, in a case where the polymer substrate is a hollow fiber or a porous membrane, a method of bringing a copolymer-containing solution obtained by dissolving the copolymer according to the present invention into contact with a cell contact portion of the hollow fiber (for example, by flowing on an inner surface (lumen) or an outer surface of the hollow fiber) and then drying coating film can be used. Incidentally, in a case where the polymer substrate is a porous membrane formed by a plurality of hollow fibers, coating with a copolymer-containing solution may be performed with respect to one hollow fiber and then the hollow fibers may be bundled, or a plurality of hollow fibers are bundled to produce a porous membrane and then the coating may be performed.

Herein, a solvent for dissolving the copolymer according to the present invention is not particularly limited as long as it can dissolve the copolymer according to the present invention. From the viewpoint of solubility of the copolymer, and the like, for example, aqueous solvents such as water, alcohols such as methanol, ethanol, propanol, or isopropanol, and polyethylene glycols; ketone-based solvents such as acetone; furan-based solvents such as tetrahydrofuran; and the like are exemplified. The solvent may be used singly or in the form of a mixture of two or more kinds thereof. Among these, in consideration of further improvement in solubility of the copolymer according to the present invention, the solvent is preferably methanol. A concentration of the copolymer in the copolymer-containing solution is not particularly limited. In consideration of the easy application to the substrate, the effects of reducing coating unevenness, and the like, the concentration thereof is preferably 0.0001 to 5% by weight more preferably 0.001 to 2% by weight.

Further, a method of coating the copolymer is not particularly limited, and a conventionally known method such as filling, dip coating (immersion method), spraying, spin coating, dropping, doctor blade, brush coating, roll coater, air knife coating, curtain coating, wire bar coating, gravure coating, or mixed solution-impregnated sponge coating can be applied.

Further, conditions for forming the coating film of the copolymer are not particularly limited. For example, a contact time of the copolymer-containing solution and the polymer substrate (for example, a time for circulating the copolymer-containing solution to a lumen or an outer surface of the hollow fiber) is preferably 1 to 5 minutes and more preferably 1 to 3 minutes, in consideration of the easy formation of the coating film (thus coating layer), the effect of reducing coating unevenness, and the like. Further, a contact temperature of the copolymer-containing solution and the polymer substrate (for example, a temperature at which the copolymer-containing solution is circulated to a lumen or an outer surface of hollow fiber) is preferably 5 to 40° C. and more preferably 15 to 30° C., in consideration of the easy formation of the coating film (thus coating layer), the effect of reducing coating unevenness, and the like.

An amount of the copolymer-containing solution applied to a surface of the polymer substrate is not particularly limited, but is preferably such an amount that a thickness of the coating layer after drying is about 0.005 to 20 μm. Incidentally, in a case where such a thickness cannot be obtainable by single contact (application), a contact (application) step (or the application step and a drying step described later) may be repeated until a desired thickness is obtainable.

With the copolymer according to the present invention, even in the case of a coating layer having a large thickness, degradation in cell proliferation activity (and further cellular adhesiveness) is suppressed. Therefore, even in a case where it is difficult to form a coating layer having a constant thickness as a cell culture substrate (cell culture vessel) having a complicated structure, favorable cell proliferation activity (and further cellular adhesiveness) can be imparted without depending on the thickness of the coating layer. Therefore, as an embodiment of the present invention, a thickness of the coating layer may be 5 to 20 μm. Further, as an embodiment of the present invention, the thickness of the coating layer may be 10 to 15 μm. According to the present invention, even in the embodiment of a thick coating layer as described above, favorable cell proliferation activity (and further cellular adhesiveness) is obtainable. Further, in a case where the thickness of the coating layer relatively increases as described above, since defects hardly occur in the coating layer (coating film) and the copolymers can overlap each other in the coating layer (coating film), a coating layer (coating film) having a high density can be formed. Therefore, the coating layer (coating film) is stably held in the surface of the cell culture substrate (cell culture vessel) so that durability is improved.

Next, by drying the coating film after the contact of the polymer substrate and the copolymer-containing solution, the coating layer (coating film) by the copolymer according to the present invention is formed on the surface of the polymer substrate. Herein, drying conditions are not particularly limited as long as the coating layer (coating film) of the copolymer according to the present invention can be formed. Specifically, a drying temperature is preferably 5 to 50° C. and more preferably 15 to 40° C. A drying step may be performed under a single condition or may be performed stepwise under different conditions. Further, a drying time is preferably 60 to 480 minutes and more preferably 120 to 360 minutes. Further, in a case where the polymer substrate is a porous membrane (hollow fiber membrane), the coating film may be dried by allowing a gas of 5 to 40° C. and more preferably 15 to 30° C. to continuously or gradually circulate on a surface of hollow fiber to which the copolymer-containing solution is applied. Herein, the gas is not particularly limited as long as it has no influence on the coating film (coating layer) and can dry the coating film. Specific examples thereof include air, an inert gas such as nitrogen gas or argon gas, and the like. Further, a circulation amount of the gas is not particularly limited as long as the coating film can be sufficiently dried. The circulation amount of the gas is preferably 5 to 150 L/min and more preferably 30 to 100 L/min.

According to such a method, the copolymer according to the present invention can be efficiently formed on the polymer substrate. Incidentally, depending on the types of cells to be proliferously grown or adhered, the polymer substrate may be further treated by a cell adhesion factor such as fibronectin, laminin, or collagen. With such a treatment, adhesion of cells to the substrate surface and growth of cells can be further promoted. In a case where the polymer substrate is a porous membrane formed of a plurality of hollow fibers, the treatment with a cell adhesion factor may be performed with respect to one hollow fiber and then the hollow fibers may be bundled, or a plurality of hollow fibers are bundled to produce a porous membrane and then the treatment may be performed. Further, the treatment with a cell adhesion factor may be performed after the coating layer containing the copolymer according to the present invention is formed, before the coating layer containing the copolymer according to the present invention is formed, or at the same time the coating layer containing the copolymer according to the present invention is formed.

<Bioreactor>

The cell culture substrate of the present invention shows excellent cell proliferation activity even when the film thickness changes (particularly, in a case where the film thickness is thick). Further, the cell culture substrate of the present invention has favorable cellular adhesiveness even when the film thickness changes (particularly, in a case where the film thickness is thick). Therefore, the cell culture substrate of the present invention can be suitably used in a bioreactor. That is, the present invention provides a bioreactor including the cell culture substrate of the present invention. Here, the bioreactor may be a plane type bioreactor or a hollow fiber type bioreactor, but is particularly preferably a hollow fiber type bioreactor. Therefore, in the following description, although a hollow fiber type bioreactor will be described as a preferred embodiment, the bioreactor of the present invention may be a plane type bioreactor, and in this case, the following embodiment can be appropriately changed and applied. Further, dimensional ratios in the drawings are exaggerated for the sake of explanatory convenience and may differ from actual ratios.

The bioreactor in which the cell culture substrate of the present invention can be suitably used is not particularly limited, but the cell culture substrate and the bioreactor of the present invention can be applied, for example, to cell culture/expansion systems described in JP 2010-523118 A (JP 5524824 B2)(WO 2008/124229 A2), JP 2013-524854 A (JP 6039547 B2) (WO 2011/140231 A1), JP 2013-507143 A (JP 5819835 B2) (WO 2011/045644 A1), JP 2013-176377 A (WO 2008/109674), JP 2015-526093 A (WO 2014/031666 A1), JP 2016-537001 A (WO 2015/073918 A1), JP 2017-509344 A (WO 2015/148704 A1), and the like; and Quantum Cell Expansion System manufactured by TERUMO BCT, INC. Conventionally, in the cell culture, facilities such as an incubator, a safety cabinet, and a clean room are separately needed, but the culture system as described above has all of those functions so that the facilities can be very simplified. Further, by controlling temperature or gas during the cell culture using the system as described above, a functionally closed system can be ensured and the cell culture can be performed automatically and in a closed environment.

Hereinafter, an embodiment of the bioreactor of the present invention will be described with reference to the drawings, but the present invention is not limited to the following embodiment.

Figure 2:
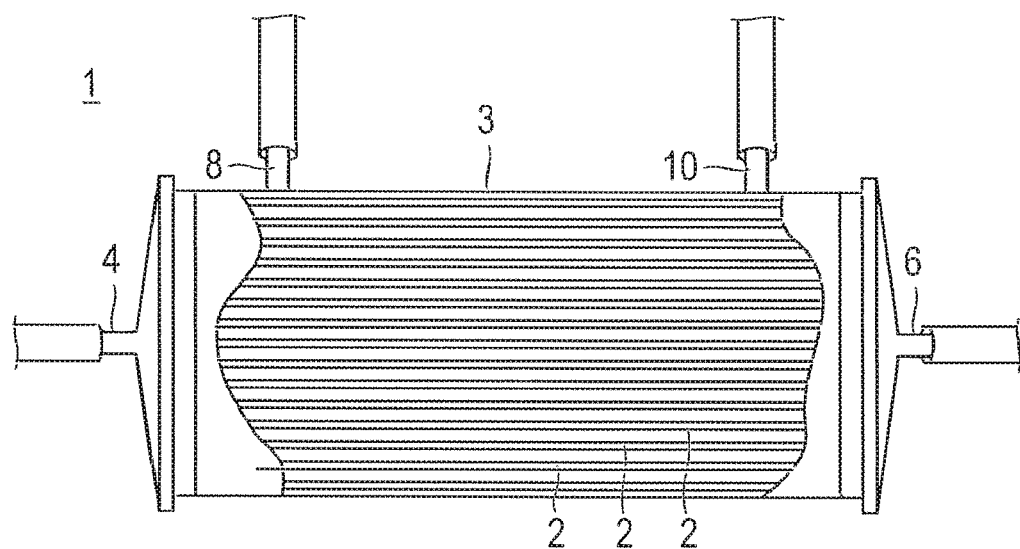
FIG. 2 is a partially cut-away side view of the bioreactor of FIG. 1.

FIG. 1 is a partial side view illustrating an embodiment of a bioreactor (hollow fiber type bioreactor) of the present invention. Further, FIG. 2 is a partially cut-away side view of the bioreactor of FIG. 1. In FIGS. 1 and 2, a bioreactor 1 has a cell culture substrate 2 of the present invention provided in a cell culture chamber 3. The cell culture chamber 3 has four openings, that is, four ports (an inlet port 4, an outlet port 6, an inlet port 8, and an outlet port 10). Herein, a culture medium including cells flows to a hollow fiber intracapillary (IC) space of the cell culture substrate 2 in the cell culture chamber 3 through the inlet port 4, and discharged from the outlet port 6. According to this, cells are efficiently adhered (attached) to and cultured on the surface of the hollow fiber lumen. Meanwhile, a culture medium or gas (such as oxygen or carbon dioxide) flows to be in contact with a hollow fiber extracapillary (EC) space of the cell culture substrate 2 in the cell culture chamber 3 through the inlet port 8, and discharged from the outlet port 10. According to this, in the cell culture chamber 3, small molecules such as culture medium components flow into the hollow fibers or unnecessary components are discharged from the inside of the hollow fibers, and cells adhered onto the surface of the hollow fibers are cultured. Further, after culturing for a predetermined time, a liquid (for example, PBS) containing trypsin is introduced into the intracapillary (IC) space of the hollow fiber of the cell culture substrate 2 in the cell culture chamber 3 through the inlet port 4, and then is held for a predetermined time (for example, about 5 to 10 minutes). Next, a culture medium or an isotonic solution such as PBS flows in the intracapillary (IC) space of the hollow fiber of the cell culture substrate 2 in the cell culture chamber 3 through the inlet port 4 to apply a shear force to cells, the cells are released from the inner wall of the hollow fiber, and the cells are recovered from the bioreactor through the outlet port 6. Incidentally, although the cells are adhered to the intracapillary (IC) space of the hollow fiber in the above embodiment, the present invention is not limited to the above embodiment, and cells may be cultured in such a manner that a culture medium containing cells flows into the outlet port 10 from the inlet port 8, the cells are efficiently adhered (attached) to an outer surface of the hollow fiber, and the culture medium flows into the outlet port 6 from the inlet port 4 in an hollow fiber lumen. Further, the fluid from the inlet port 4 into the outlet port 6 may flow in either a co-current or counter-current direction with respect to flow of fluid into the outlet port 10 from the inlet port 8.

[Use of Bioreactor]

As mentioned above, the bioreactor of the present invention includes a cell culture substrate excellent in cell proliferation activity (and further cellular adhesiveness). Herein, cells which can be cultured in the bioreactor of the present invention may be adherent (scaffold-dependent) cells, non-adherent cells, or any combination thereof, but the bioreactor of the present invention can be particularly suitably used in culturing of adherent (scaffold-dependent) cells since it has also excellent cellular adhesiveness (and further cell proliferation activity). Herein, as the adherent (scaffold-dependent) cells, there are animal cells such as stem cells including mesenchymal stem cell (MSC) or the like, fibroblast cells, and the like. As mentioned above, attention has been paid to stem cells in development of regenerative medicine or drug discovery. Therefore, the bioreactor of the present invention can be suitably used in culturing of stem cells. That is, the present invention provides a method for culturing a stem cell using the bioreactor of the present invention. Herein, the method for culturing a stem cell is not particularly limited, and a general culturing method can be applied similarly or appropriately modified.

EXAMPLES

The effects of the present invention will be described using the following examples and comparative examples. However, the technical scope of the present invention is not limited to only the following examples. Incidentally, in the following examples, operations were carried out at room temperature (25° C.) unless otherwise specified. In addition, unless otherwise specified, "%" and "part" mean "% by weight" and "parts by weight," respectively.

Production Example 1: Synthesis of Copolymer (1)

To a 20-ml glass pressure-proof test tube, 1.05 g (0.0073 mol) of carboxyethyl acrylate (CEA), 0.95 g (0.0073 mol) of hydroxyethyl methacrylate (HEMA), and 3 g of ethanol were added, and then nitrogen gas was bubbled for 10 seconds, thereby preparing a monomer solution (1). To this monomer solution (1), 0.004 g (0.013 mmol) of 2,2'-azobis (4-methoxy-2,4-dimethylvaleronitrile) as a polymerization initiator was added, and the resultant mixture was heated in a heat block set at 45° C. for 6 hours, to perform polymerization reaction, thereby obtaining obtain a polymerization liquid (1). This polymerization liquid (1) was added to 50 ml of n-hexane, and the precipitated polymer component was recovered and dried under reduced pressure, thereby obtaining a copolymer of carboxyethyl acrylate and hydroxyethyl methacrylate (CEA:HEMA=50:50 (molar ratio)) (copolymer (1)).

Production Example 2: Synthesis of Copolymer (2)

To a 20-ml glass pressure-proof test tube, 1.24 g (0.0086 mol) of carboxyethyl acrylate (CEA), 0.76 g (0.0058 mol) of hydroxyethyl methacrylate (HEMA), and 3 g of ethanol were added, and then nitrogen gas was bubbled for 10 seconds, thereby preparing a monomer solution (2). To this monomer solution (2), 0.004 g (0.013 mmol) of 2,2'-azobis (4-methoxy-2,4-dimethylvaleronitrile) as a polymerization initiator was added, and the resultant mixture was heated in a heat block set at 45° C. for 6 hours, to perform polymerization reaction, thereby obtaining a polymerization liquid (2). This polymerization liquid (2) was added to 50 ml of n-hexane, and the precipitated polymer component was recovered and dried under reduced pressure, thereby obtaining a copolymer of carboxyethyl acrylate and hydroxyethyl methacrylate (CEA:HEMA=60:40 (molar ratio)) (copolymer (2)).

Production Example 3: Synthesis of Copolymer (3)

To a 20-ml glass pressure-proof test tube, 1.63 g (0.0113 mol) of carboxyethyl acrylate (CEA), 0.37 g (0.0028 mol) of hydroxyethyl methacrylate (HEMA), and 3 g of ethanol were added, and then nitrogen gas was bubbled for 10 seconds, thereby preparing a monomer solution (3). To this monomer solution (3), 0.004 g (0.013 mmol) of 2,2'-azobis(4-methoxy-2,4-dimethylvaleronitrile) as a polymerization initiator was added, and the resultant mixture was heated in a heat block set at 45° C. for 6 hours, to perform polymerization reaction, thereby obtaining a polymerization liquid (3). This polymerization liquid (3) was added to 50 ml of n-hexane, and the precipitated polymer component was recovered and dried under reduced pressure, thereby obtaining a copolymer of carboxyethyl acrylate and hydroxyethyl methacrylate (CEA:HEMA=80:20 (molar ratio)) (copolymer (3)).

Production Example 4: Synthesis of Copolymer (4)

To a 20-ml glass pressure-proof test tube, 1.80 g (0.0125 mol) of carboxyethyl acrylate (CEA), 0.20 g (0.0015 mol) of hydroxyethyl methacrylate (HEMA), and 3 g of ethanol were added, and then nitrogen gas was bubbled for 10 seconds, thereby preparing a monomer solution (4). To this monomer solution (4), 0.004 g (0.013 mmol) of 2,2'-azobis(4-methoxy-2,4-dimethylvaleronitrile) as a polymerization initiator was added, and the resultant mixture was heated in a heat block set at 45° C. for 6 hours, to perform polymerization reaction, thereby obtaining a polymerization liquid (4). This polymerization liquid (4) was added to 50 ml of n-hexane, and the precipitated polymer component was recovered and dried under reduced pressure, thereby obtaining a copolymer of carboxyethyl acrylate and hydroxyethyl methacrylate (CEA:HEMA=90:10 (molar ratio)) (copolymer (4)).

Production Example 5: Synthesis of Copolymer (5)

To a 20-ml glass pressure-proof test tube, 0.85 g (0.0059 mol) of carboxyethyl acrylate (CEA), 1.15 g (0.0088 mol) of hydroxyethyl methacrylate (HEMA), and 3 g of ethanol were added, and then nitrogen gas was bubbled for 10 seconds, thereby preparing a monomer solution (5). To this monomer solution (5), 0.004 g (0.013 mmol) of 2,2'-azobis(4-methoxy-2,4-dimethylvaleronitrile) as a polymerization initiator was added, and the resultant mixture was heated in a heat block set at 45° C. for 6 hours, to perform polymerization reaction, thereby obtaining a polymerization liquid (5). This polymerization liquid (5) was added to 50 ml of n-hexane, and the precipitated polymer component was recovered and dried under reduced pressure, thereby obtaining a copolymer of carboxyethyl acrylate and hydroxyethyl methacrylate (CEA:HEMA=40:60 (molar ratio)) (copolymer (5)).

Production Example 6: Synthesis of MEA Polymer (6)

To a 20-ml glass pressure-proof test tube, 2.0 g (0.0154 mol) of methoxyethyl acrylate (MEA) and 3 g of methanol were added, and then nitrogen gas was bubbled for 10 seconds, thereby preparing a monomer solution (6). To this monomer solution (6), 0.004 g (0.013 mmol) of 2,2'-azobis(4-methoxy-2,4-dimethylvaleronitrile) as a polymerization initiator was added, and the resultant mixture was heated in a heat block set at 45° C. for 6 hours, to perform polymerization reaction, thereby obtaining a polymerization liquid (6). This polymerization liquid (6) was added to 50 ml of ethanol, and the precipitated polymer component was recovered and dried under reduced pressure, thereby obtaining a homopolymer of methoxyethyl acrylate (MEA polymer (6)).

Production Example 7: Synthesis of HEMA Polymer (7)

To a 20-ml glass pressure-proof test tube, 2.0 g (0.0154 mol) of hydroxyethyl methacrylate (HEMA) and 3 g of methanol were added, and then nitrogen gas was bubbled for 10 seconds, thereby preparing a monomer solution (7). To this monomer solution (7), 0.004 g (0.013 mmol) of 2,2'-azobis(4-methoxy-2,4-dimethylvaleronitrile) as a polymerization initiator was added, and the resultant mixture was heated in a heat block set at 45° C. for 6 hours, to perform polymerization reaction, thereby obtaining a polymerization liquid (7). This polymerization liquid (7) was added to 50 ml of n-hexane, and the precipitated polymer component was recovered and dried under reduced pressure, thereby obtaining a homopolymer of hydroxyethyl methacrylate (HEMA polymer (7)).

Production Example 8: Synthesis of CEA Polymer (8)

To a 20-ml glass pressure-proof test tube, 2.0 g (0.0139 mol) of carboxyethyl acrylate (CEA) and 3 g of ethanol were added, and then nitrogen gas was bubbled for 10 seconds, thereby preparing a monomer solution (8). To this monomer solution (8), 0.004 g (0.013 mmol) of 2,2'-azobis(4-methoxy-2,4-dimethylvaleronitrile) as a polymerization initiator was added, and the resultant mixture was heated in a heat block set at 45° C. for 6 hours, to perform polymerization reaction, thereby obtaining a polymerization liquid (8). This polymerization liquid (8) was added to 50 ml of n-hexane, and the precipitated polymer component was recovered and dried under reduced pressure, thereby obtaining a homopolymer of carboxyethyl acrylate (CEA polymer (8)).

Example 1-1: Coating to Cell Culture Dish

The copolymer (1) obtained in Production Example 1 described above was dissolved in methanol to have a concentration of 1.0% by weight, thereby producing a coating liquid (1-1). 50 µL of this coating liquid (1-1) was added to each well of commercially available 96-well tissue culture polystyrene dish (without a plasma treatment, manufactured by FALCON, trade name: Non-Tissue Culture Treated Plate, 96 Well, Flat Bottom with Low Evaporation Lid) and dried at 20° C. for 360 minutes to produce a polymer coating film (dry thickness: 13 µm) on a well surface, thereby obtaining a cell culture dish (1-1).

Example 1-2: Coating to Cell Culture Dish

The copolymer (1) obtained in Production Example 1 described above was dissolved in methanol to have a concentration of 0.005% by weight, thereby preparing a coating liquid (1-2). 25 µL of the coating liquid (1-2) was added to each well of commercially available 96-well tissue culture polystyrene dish (without a plasma treatment, manufactured by FALCON, trade name: Non-Tissue Culture Treated Plate, 96 Well, Flat Bottom with Low Evaporation Lid), and dried at 20° C. for 360 minutes to produce a polymer coating film (dry thickness: 0.030 µm) on a well surface, thereby obtaining a cell culture dish (1-2).

Examples 2-1 to 4-1: Coating to Cell Culture Dish

A polymer coating film was produced on a well surface according to the similar method to Example 1-1, except that, in Example 1-1, each of the copolymers (2) to (4) was used instead of the copolymer (1), thereby obtaining cell culture dishes (2-1) to (4-1).

Examples 2-2 to 4-2: Coating to Cell Culture Dish

A polymer coating film was produced on a well surface according to the similar method to Example 1-2, except that, in Example 1-2, each of the copolymers (2) to (4) was used instead of the copolymer (1), thereby obtaining cell culture dishes (2-2) to (4-2).

Comparative Examples 1-1 to 4-1: Coating to Cell Culture Dish

A polymer coating film was produced on a well surface according to the similar method to Example 1-1, except that, in Example 1-1, each of the copolymer (5), the MEA polymer (6), the HEMA polymer (7), and the CEA polymer (8) was used instead of the copolymer (1), thereby obtaining comparative cell culture dishes (1-1) to (4-1).

Comparative Examples 1-2 to 4-2: Coating to Cell Culture Dish

A polymer coating film was produced on a well surface according to the similar method to Example 1-2, except that, in Example 1-2, each of the copolymer (5), the MEA polymer (6), the HEMA polymer (7), and the CEA polymer (8) was used instead of the copolymer (1), thereby obtaining comparative cell culture dishes (1-2) to (4-2).

Reference Example 1

A commercially available 96-well tissue culture polystyrene dish (without a plasma treatment and a polymer coating film, manufactured by FALCON, trade name: Non-Tissue Culture Treated Plate, 96 Well, Flat Bottom with Low Evaporation Lid) was used as a non-treated cell culture dish.

[Evaluation 1: Cell Culture and Measurement of Proliferation Activity]

Cells were cultured using the cell culture dishes (1-1) to (4-1), and (1-2) to (4-2), the comparative cell culture dishes (1-1) to (4-1), and (1-2) to (4-2) obtained in Examples 1-1 to 4-1 and 1-2 to 4-2 and Comparative Examples 1-1 to 4-1 and 1-2 to 4-2, and the non-treated cell culture dish as Reference Example 1, and the cell-proliferative activity (cell proliferation activity) was evaluated. Incidentally, as the cells, human adipose tissue-derived mesenchymal stem cells (Lonza, Walkersville, Md., U.S.A.) were used. The donor was a 22-year-old man and expressed CD13, CD29, CD44, CD73, CD90, CD105, CD166≥90%, CD14, CD31, and CD45≤5%.

The human adipose tissue-derived mesenchymal stem cells were seeded on each well of each cell culture dish to be $1 \times 10^3$ cells/well, and then cultured for three days in Mesenchymal Stem Cell Growth Medium 2 (PromoCell GmbH, Bedford, Mass., U.S.A.) in an incubator under humidified conditions at 37° C. in the presence of 5% $CO_2$. After the completion of culture, the culture solution was exchanged with Mesenchymal Stem Cell Growth Medium 2 containing 10% WST-1 (Premix WST-1 Cell Proliferation Assay System, Takara Bio Inc., Shiga, Japan) and then incubated for about 6 hours under normal pressure (37° C., 5% $CO_2$) under the humidified conditions. An absorbance (450 nm, comparison 600 nm) of the culture solution was measured by a microplate reader and regarded as cell-proliferative activity. Results are presented in the following Table 1.

[Evaluation 2: Cell Culture and Measurement of Adhesion Activity]

Cells were cultured using the cell culture dishes (1-1) to (4-1), and (1-2) to (4-2), the comparative cell culture dishes (1-1) to (4-1) and (1-2) to (4-2) obtained in Examples 1-1 to 4-1 and 1-2 to 4-2 and Comparative Examples 1-1 to 4-1 and 1-2 to 4-2, and the non-treated cell culture dish as Reference Example 1, and the cell adhesion activity (cellular adhesiveness) was evaluated. Incidentally, as the cells, human adipose tissue-derived mesenchymal stem cells (Lonza, Walkersville, Md., U.S.A.) were used. The donor was a 22-year-old man and expressed CD13, CD29, CD44, CD73, CD90, CD105, CD166≥90%, CD14, CD31, and CD45≤5%.

The human adipose tissue-derived mesenchymal stem cells were seeded on each well of each cell culture dish to be $2 \times 10^3$ cells/well, and then cultured for one day in Mesenchymal Stem Cell Growth Medium 2 (PromoCell GmbH, Bedford, Mass., U.S.A.) in an incubator under humidified conditions at 37° C. in the presence of 5% $CO_2$. After the completion of culture, the culture solution was exchanged with Mesenchymal Stem Cell Growth Medium 2 containing 10% WST-1 (Premix WST-1 Cell Proliferation Assay System, Takara Bio Inc., Shiga, Japan) and then incubated for about 4 hours under normal pressure (37° C., 5% $CO_2$) under humidified conditions. An absorbance (450 nm, comparison 600 nm) of the culture solution was measured by a microplate reader and regarded as cell adhesion activity. Results are presented in the following Table 2.

TABLE 1

| | Polymer | | Cell-proliferative activity ($Abs_{450}$) | | | |
|---|---|---|---|---|---|---|
| | Monomer | Monomer composition | Thickness: 13 μm | | Thickness: 0.030 μm | |
| | Monomer type | (Molar ratio) | | ($Abs_{450}$) | | ($Abs_{450}$) |
| Copolymer (1) | CEA-HEMA | 50:50 | Example 1-1 | 0.148 | Example 1-2 | 0.144 |
| Copolymer (2) | CEA-HEMA | 60:40 | Example 2-1 | 0.151 | Example 2-2 | 0.147 |
| Copolymer (3) | CEA-HEMA | 80:20 | Example 3-1 | 0.175 | Example 3-2 | 0.164 |
| Copolymer (4) | CEA-HEMA | 90:10 | Example 4-1 | 0.173 | Example 4-2 | 0.162 |
| Copolymer (5) | CEA-HEMA | 40:60 | Comparative Example 1-1 | 0.045 | Comparative Example 1-2 | 0.155 |
| MEA polymer (6) | MEA | — | Comparative Example 2-1 | 0.030 | Comparative Example 2-2 | 0.157 |
| HEMA polymer (7) | HEMA | — | Comparative Example 3-1 | 0.030 | Comparative Example 3-2 | 0.129 |
| CEA polymer (8) | CEA | — | Comparative Example 4-1 | 0.100 | Comparative Example 4-2 | 0.135 |
| (Without plasma treatment and without polymer coating film) | | | — | | 0.100 | |

TABLE 2

| | Polymer | | Cell adhesion activity ($Abs_{450}$) | | | |
|---|---|---|---|---|---|---|
| | Monomer type | Monomer composition (Molar ratio) | Thickness: 13 μm | | Thickness: 0.030 μm | |
| Copolymer (1) | CEA-HEMA | 50:50 | Example 1-1 | 0.051 | Example 1-2 | 0.052 |
| Copolymer (2) | CEA-HEMA | 60:40 | Example 2-1 | 0.082 | Example 2-2 | 0.050 |
| Copolymer (3) | CEA-HEMA | 80:20 | Example 3-1 | 0.089 | Example 3-2 | 0.056 |
| Copolymer (4) | CEA-HEMA | 90:10 | Example 4-1 | 0.081 | Example 4-2 | 0.059 |
| Copolymer (5) | CEA-HEMA | 40:60 | Comparative Example 1-1 | 0.045 | Comparative Example 1-2 | 0.053 |
| MEA polymer (6) | MEA | — | Comparative Example 2-1 | 0.032 | Comparative Example 2-2 | 0.06 |
| HEMA polymer (7) | HEMA | — | Comparative Example 3-1 | 0.024 | Comparative Example 3-2 | 0.047 |
| CEA polymer (8) | CEA | — | Comparative Example 4-1 | 0.083 | Comparative Example 4-2 | 0.051 |
| (Without plasma treatment and without polymer coating film) | | | Reference Example 1 | 0.049 | | |

It is noted from the result of the cell proliferation activity evaluation by the absorbance ($Abs_{450}$) presented in the above Table 2, the cell culture dishes having the polymer coating films of the copolymers (1) to (4) of Production Examples 1 to 4 formed thereon exhibited excellent cell proliferation activity even in the case of the film thickness being thick. Therefore, based on the above description, it can be said that the film thickness dependence of the cell proliferation activity of the copolymers (1) to (4) of Production Examples 1 to 4 is small. Further, of them, regarding the copolymers (3) and (4), the value of absorbance ($Abs_{450}$) when the film thickness is large is large, and this indicates that the number of cells obtained by culturing is the largest. In addition, from the result of the above Table 2, the cell culture dishes having the polymer coating films of the copolymers (1) to (4) of Production Examples 1 to 4 formed thereon exhibited favorable cellular adhesiveness even in the case of the film thickness being thick. That is, it can be said that the film thickness dependence of the cellular adhesiveness of the copolymers (1) to (4) of Production Examples 1 to 4 is small as well.

On the other hand, it was shown that the cell culture dishes in which the polymer coating films are formed using the CEA-HEMA copolymer, the MEA polymer (6), the HEMA polymer (7), and the CEA polymer (8) which are out of the composition according to the present invention had a high absorbance ($Abs_{450}$) and exhibited favorable cell proliferation activity when the film thickness is thin, but when the film thickness increases, each absorbance ($Abs_{450}$) was lowered and cell proliferation activity was degraded. It is worthy of special note that although the copolymer (5) used in Comparative Example 1-1 does not have a large difference in the composition (molar ratio) of the structural units (1) and (2) as compared to the copolymer (1) used in Example 1-1, the absorbance ($Abs_{450}$) presented in the above Table 1 is greatly lowered (a large difference in cell-proliferative activity is recognized). The reason for this is presumed that when the thickness of the coating layer (coating film) increases, the influence of the hardness of the copolymer is significantly shown.

REFERENCE SIGNS LIST

1 BIOREACTOR
2 CELL CULTURE SUBSTRATE
3 CELL CULTURE CHAMBER
4, 8 INLET PORT
6, 10 OUTLET PORT

The invention claimed is:

1. A cell culture substrate comprising a coating layer on at least one surface of a polymer substrate,
wherein the coating layer includes a copolymer consisting of more than 45% by mole or more and 98% by mole or less of a structural unit (1) and 2% by mole or more and 55% by mole or less of a structural unit (2),
wherein the structural unit (1) comprises a carboxyl group and is derived from a carboxyalkyl acrylate monomer represented by Formula (1):

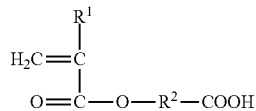

wherein $R^1$ represents a hydrogen atom or a methyl group and $R^2$ represents an alkylene group having 2 or 3 carbon atoms, and
wherein the structural unit (2) comprises a hydroxyl group and is derived from an ethylenically unsaturated monomer comprising an acryloyl group and a hydroxyl group.

2. The cell culture substrate according to claim 1, wherein the copolymer consists of by mole or more and 90% by mole or less of the structural unit (1) and 10% by mole or more and 40% by mole or less of the structural unit (2).

3. The cell culture substrate according to claim 1, wherein the ethylenically unsaturated monomer is hydroxyalkyl acrylate represented by following Formula (2):

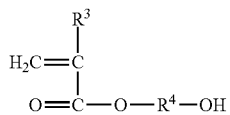

wherein $R^3$ represents a hydrogen atom or a methyl group and $R^4$ represents an alkylene group having 2 or 3 carbon atoms.

4. The cell culture substrate according to claim 1, wherein the polymer substrate is a porous membrane.

5. A bioreactor comprising the cell culture substrate according claim 1.

6. A method for culturing a stem cell using the bioreactor according to claim 5.

7. The cell culture substrate according to claim 2, wherein the ethylenically unsaturated monomer is hydroxyalkyl acrylate represented by following Formula (2):

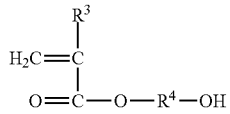

wherein $R^3$ represents a hydrogen atom or a methyl group and $R^4$ represents an alkylene group having 2 or 3 carbon atoms.

8. The cell culture substrate according to claim 1, wherein the ethylenically unsaturated monomer is selected from the group consisting of hydroxyethyl acrylate, hydroxypropyl acrylate, hydroxyisopropyl acrylate, hydroxyethyl methacrylate, hydroxypropyl methacrylate, hydroxyisopropyl methacrylate, and combinations thereof.

9. The cell culture substrate according to claim 1, wherein the carboxyalkyl acrylate monomer represented by Formula (1) is selected from the group consisting of carboxypropyl acrylate, carboxyisopropyl acrylate, carboxyethyl methacrylate, carboxypropyl methacrylate, carboxy isopropyl methacrylate, and combinations thereof.

10. The cell culture substrate according to claim 1, wherein the coating layer consists of the copolymer.

* * * * *